United States Patent [19]

Picarelli

[11] Patent Number: 5,817,523
[45] Date of Patent: Oct. 6, 1998

[54] METHOD AND KIT FOR CONFIRMING IN VITRO DIAGNOSIS OF COELIAC DISEASE

[76] Inventor: Antonio Picarelli, Via Cesare Pavese, 173, 00144 Rome, Italy

[21] Appl. No.: 898,865

[22] Filed: Jul. 23, 1997

[30] Foreign Application Priority Data

Jul. 24, 1996 [IT] Italy ..................... RAM96 A 000523
Mar. 10, 1997 [IT] Italy ..................... RM97 A 000133

[51] Int. Cl.$^6$ ................................. G01N 33/567
[52] U.S. Cl. ..................... 436/503; 436/513; 436/518; 436/519; 436/547; 435/7.21; 435/975
[58] Field of Search .................. 424/9.1, 130.1, 424/139.1, 144.1, 142.1, 171.1, 184.1, 185.1, 551, 804, 810; 435/7.1, 7.2, 325, 326, 331, 975, 7.21; 436/503, 513, 547, 518, 519; 530/300, 328, 330, 372, 374, 843, 844, 861

[56] References Cited

PUBLICATIONS

Ferreira et al. Endomysial antibody: is it the best screening test for coeliac disease? Gut 33:1633–1637, 1992.
Lerner et al. Immunological diagnosis of childhood coeliac disease: comparison between antigliadin, antireticulin, and antiendomysial antibodies, Clin. Exp. Immunol. 95:78–82, 1994.
Vazquez et al. Screening for asymptomatic celiac sprue in families, J. Clin. Gastroenterol. 21:130–133, 1995.
Vogelsang et al. Screening for celiac disease: a prospective study on the value of noninvasive tests, 90:394–398, 1995.
Ascher et al. A new laboratory kit for antigliadin IgA at diagnosis and follow–up of childhood celiac disease, J. Pediatric Gastroenterol. 10:443–450, 1990.
Devine et al. Screening and monitoring coeliac disease: multicentre trial of a new serum antibody test kit, Disease Markers 12:71–80, 1994.
Berger et al. Evaluation of six anti–gliadin antibody assays, J. Immunol. Methods 191:77–86, 1986.

*Primary Examiner*—Patricia Duffy
*Assistant Examiner*—Susan Pellegrino
*Attorney, Agent, or Firm*—Stevens, Davis, Miller & Mosher, L.L.P.

[57] ABSTRACT

In order to diagnose the coeliac disease antiendomysial antibodies are detected through immunofluorescence techniques in culture media in which bioptic fragments of the human enteral mucosa are kept alive. The cultures of the enteral mucosa take place by dipping the bioptic fragment into nutrient liquids with or without the presence of low concentrations of peptic-tryptic digest of gliadin. The peptide fragment of gliadin containing a definite aminoacid sequence capable of production of antiendomysial antibodies to a greater extent than the PT digest, even in very little concentration, is also identified.

8 Claims, No Drawings

METHOD AND KIT FOR CONFIRMING IN VITRO DIAGNOSIS OF COELIAC DISEASE

FIELD OF THE INVENTION

The present invention relates to the diagnosis in vitro of specific pathologies of the coeliac disease. More particularly the invention relates to a method and a kit for confirming the diagnosis of the coeliac disease through the detection of antiendomysial antibodies in culture media in which bioptic fragments of the human enteral mucosa in contact with gliadin and particularly with a peptide of gliadin, identified as the peptide of position 31–43 of the aminoacid sequence of such protein, are kept alive.

The invention also relates to the use of the peptide of gliadin of position 31–43 in the production of antiendomysial antibodies in a medium for organ culture.

BACKGROUND OF THE INVENTION

The coeliac disease is a common gastroenterologic pathology, the diagnosis of which is made by a histologic test of an enteral biopsy.

The diagnosis is currently carried out by the examination of the enteral structure which is typically of the villar type: if mucosa is diseased, it is essentially flat, i.e. without villi normally present in a sound mucosa. In other words, such pathology brings to a subtotal atrophy of the enteral mucosa.

The typical lesions of the coeliac disease are supposed not to be diffused in an organ such as small intestine which is more than 6 meters long but positioned in confined areas. Therefore, the histologic test can provide non-real data as the bioptic fragments can be taken from non-atrophic parts.

Moreover it has been recently demonstrated (Picarelli et al., Gastroenterology 1996, in press) that the coeliac disease can be diagnosed even without the typical histologic enteral lesions. This is possible by an immunohistochemical examination of the enteral mucosa which is capable of detecting the presence of specific immunological markers, for example CD 25 or ICAM 1. However, such technique is very difficult and sophisticated.

It is also known that the antigen responsible for the disease is gluten which is a protein contained in some cereals.

It has been further demonstrated that by subjecting bioptic fragments of patients in remission to said antigen in an organ culture, said fragments show specific immunological markers of such a pathology which can be displayed during the phase of acclaimed disease (Maiuri, Picarelli et al., Gastroenterology, May 1996).

It is also known that antiendomysial antibodies (EMA) have high sensitivity and specificity both as screening means and test means to follow the disease during the treatment.

It is needed from the foregoing to provide and/or to develop means for the diagnosis in vitro in addition to the histologic test of the enteral mucosa so as to detect, to confirm and/or to exclude a coeliac disease.

SUMMARY OF THE INVENTION

The inventor started from the fact that it is possible to cultivate bioptic fragments of enteral mucosa according to an already known method (Picarelli et al., Gastroenterology 1996, in press), however, of particular difficulty which needs laboratory equipment with such technical requirements that cannot be easily found.

The present invention seeks to overcome such problems without resorting to particularly difficult and sophisticated methods but by providing an effective method and kit for diagnosing the coeliac disease in a very easy manner.

It was surprisingly found that it is possible to cultivate enteral mucosa without resorting to particular methods. According to a first feature of the described invention, a culture of bioptic fragments is carried out only by dipping the same into an adapted culture liquid medium.

In the course of the study, it was also proved that:
1) enteral mucosa of subjects who are or have been affected by coeliac disease produces antiendomysial antibodies in the presence of gliadin, a protein of gluten;
2) enteral mucosa of sick subjects produces antibodies even without gliadin;
3) enteral mucosa of subjects who are sound and/or affected by other pathologies, however, does not produce any antiendomysial antibody.

Therefore, the inventor came to the conclusion that the possible presence of antiendomysial antibodies (EMA) in liquids can be detected by typical immunofluorescence techniques upon dipping enteral mucosa fragments into suitable nutrient liquids containing gliadin.

As such (EMA) antibodies appear only if the mucosa belongs to patients who are or have been sick, such a method may be used as diagnosis confirmation test for coeliac disease.

DETAILED DESCRIPTION OF THE PREFERRED EMBODIMENT

According to the invention, the technique for carrying out such a method essentially provides the following steps before the immunofluorescence:

taking bioptic fragments of enteral mucosa;

cultivating enteral mucosa in a plain medium for the control; and cultivating enteral mucosa in a medium with the addition of PT (Peptic-Tryptic Digest of gliadin).

Said cultures take place by only dipping bioptic fragments into test tubes containing an amount of culture medium between 100 and 1000 microliters ($\mu$l) The culture time is between 24 and 72 hours under a sterile atmosphere of 95% oxygen and 5% carbon dioxide and at a controlled temperature of 37° C.

The composition of the medium is that commonly used in the organ or cellular cultures. A preferred medium has by way of example the following composition:

| | |
|---|---|
| Trowel | 13 ml |
| NCTC | 4 ml |
| Glutamine | 200 $\mu$l |
| Foetal vitellus serum | 3 ml |
| Penicillin-Streptomycin | 2 ml |
| Gentamicin | 40 $\mu$l |
| total pH | 7,4 (7,2 + 7,5) |

The presence of EMA antibodies was detected in both culture media of bioptic fragments with or without gliadin after 24 and 48 hours by a monkey oesophagus immunofluorescence technique.

The achieved results with a group of 33 patients, 10 sick, 10 sound, and 13 in remission, are shown in the following table:

| Sick<br>positive EMA | Cured<br>positive EMA | Control<br>positive EMA | |
|---|---|---|---|
| 10/10 | 0/13 | 0/10 | culture° |
| 10/10 | 9/13 | 0/10 | gliadin° |
| 10/10 | 13/13 | 0/10 | gliadin* |

°24 hours of incubation with plain culture
*48 hours of incubation with gliadin.

It should be appreciated from the table that the test is capable of detecting the coeliac disease in all of the sick subjects and in about 70% of the subjects in remission. After 48 hours the disease is detected in 100% of the patients, also those in remission. The test kit used in such a diagnostic method described above includes:

a test tube containing culture medium of the organ culture type;

a test tube containing the same culture medium as above with the addition of 1 mg/ml of PT;

two glasses with a section of monkey oesophagus;

a secondary antihuman IGA antibody treated with fluorescin;

washing liquids (PBS—Phosphate Buffer Solution);

two cover glasses.

Although such a method is very easy to carry out, however, it has the drawback that the concentrations of the peptic-tryptic digest of gliadin in the culture medium needed for producing antibodies are very high, i.e. 1 mg/ml.

Considering that the high concentration of digest in the medium was due to the fact that only a few fragments of gliadin were toxic, i.e. capable of producing antiendomysial antibodies, a number of fragments of the aminoacid sequence of gliadin were activated in the human intestine both in vivo and in vitro. Thus, it was surprisingly found that the toxic aminoacid sequence is GLN-GLN-GLN-PRO (SEQ ID NO: 1) which is contained in the peptide of position 31–43 and such peptide is capable of production of antiendomysial antibodies to a greater extent than the peptic-tryptic digest of gliadin, even with very low concentrations between 0.005 and 0.1 mg/ml. Of course, this facilitates by far the proposed method and lowers the cost.

The aminoacid sequence of the peptide of position 31–43 is as follows: LEU-GLY-GLN-GLN-GLN-PRO-PHE-PRO-PRO-GLN-GLN-PRO-TYR (SEQ ID NO: 2).

It is self-evident that the choice of the peptide of position 31–43 is significant on the ground both of economy and specificity as it is the shortest fragment containing the aminoacid sequence responsible for the immunological action. Moreover, it is obvious that peptide fragments of gliadin greater than 31–43 fragments may be used with not dissimilar results. Therefore, it is a further object of the present invention to provide a method of the above-mentioned type including the following steps:

taking bioptic fragments of enteral mucosa;

cultivating firstly enteral mucosa in a plain medium for the control; and cultivating secondly enteral mucosa in a medium with the addition of a peptide fragment of gliadin containing the aminoacid sequence GLN-GLN-GLN-PRO (SEQ ID NO: 1);

taking both culture media and detecting the present anti-endomysial antibodies.

It is still an object of the present invention to provide a method of the above-mentioned type wherein the used peptide fragment of gliadin is the peptide of gliadin of position 31–43, the aminoacid sequence of which is LEU-GLY-GLN-GLN-GLN-PRO-PHE-PRO-PRO-GLN-GLN-PRO-TYR (SEQ ID NO: 2).

It is a further object of the invention to provide a kit used for carrying out the diagnostic method described above, including:

a test tube containing culture medium of the organ culture type;

a test tube containing the same culture medium as above with the addition of the peptide of gliadin of position 31–43, the aminoacid sequence of which is LEU-GLY-GLN-GLN-GLN-PRO-PHE-PRO-PRO-GLN-GLN-PRO-TYR (SEQ ID NO: 2), in the amount of 0.005–0.1 mg/ml;

two glasses with a section of monkey oesophagus;

a secondary antihuman IGA antibody treated with fluorescin;

washing liquids (PBS—Phosphate Buffer Solution);

two cover glasses.

I claim:

1. A method of diagnosing coeliac disease in vitro comprising the following steps:
    a) taking bioptic fragments of enteral mucosa from the distal duodenum by gastroscopy;
    b) adding a first bioptic fragment into a first organ culture medium to form a first bioptic culture;
    c) adding a second bioptic fragment into a second organ culture medium containing a peptic tryptic digest of gliadin to form a second bioptic culture;
    d) incubating said first and second bioptic cultures;
    e) removing a sample of the first incubated culture medium and the second incubated culture medium;
    f) subjecting the first and the second culture media samples to a monkey oesophagus immunofluorescence technique for antiendomysial antibodies; and
    g) where the presence of antiendomysial antibodies in either the first or second culture media samples is indicative of coeliac disease.

2. The method of claim 1, wherein said incubation comprises incubating said cultures for a time between 24 and 72 hours at a temperature of about 37° C. under sterile atmosphere of 95% oxygen and 5% $CO_2$.

3. A method of diagnosing coeliac disease in vitro comprising the following steps:
    a) taking bioptic fragments of enteral mucosa from the distal duodenum by gastroscopy;
    b) adding a first bioptic fragment into a first organ culture medium to form a first bioptic culture;
    c) adding a second bioptic fragment into a second organ culture medium containing a peptide fragment of gliadin containing the amino acid sequence GLN-GLN-GLN-PRO (SEQ ID NO: 1) to form a second bioptic culture;
    d) incubating said first and second bioptic cultures;
    e) removing a sample of the first incubated culture medium and the second incubated culture medium;
    f) subjecting the first and the second culture media samples to a monkey oesophagus immunofluorescence technique for antiendomysial antibodies; and
    g) where the presence of antiendomysial antibodies in either the first or second culture media samples is indicative of coeliac disease.

4. The method of claim 3, wherein said incubation comprises incubating said cultures for a time between 24 and 72 hours at a temperature of about 37° C. under sterile atmosphere of 95% oxygen and 5% $CO_2$.

5. A method of diagnosing coeliac disease in vitro comprising the following steps:
    a) taking bioptic fragments of enteral mucosa from the distal duodenum by gastroscopy;
    b) adding a first bioptic fragment into a first organ culture medium to form a first bioptic culture;
    c) adding a second bioptic fragment into a second organ culture medium containing a peptide fragment of gliadin containing the amino acid sequence LEU-GLY-GLN-GLN-GLN-PRO-PHE-PRO-PRO-GLN-GLN-PRO-TYR (SEQ ID NO:2) of gliadin to form a second bioptic culture;
    d) incubating said first and second bioptic cultures;
    e) removing a sample of the first incubated culture medium and the second incubated culture medium;
    f) subjecting the first and the second culture media samples to a monkey oesophagus immunofluorescence technique for antiendomysial antibodies; and
    g) where the presence of antiendomysial antibodies in either the first or second culture media samples is indicative of coeliac disease.

6. The method of claim 5, wherein said incubation comprises incubating said cultures for a time between 24 and 72 hours at a temperature of about 37° C. under sterile atmosphere of 95% oxygen and 5% $CO_2$.

7. A kit for the diagnosis in vitro of the coeliac disease, comprising:
    a test tube containing culture medium of the organ culture type;
    a test tube containing the same culture medium as above with the addition of 1 mg/ml of PT (peptic-tryptic digest of gliadin);
    two glass slides with a section of monkey oesophagus;
    a secondary antihuman IGA antibody treated with fluorescin;
    washing liquids (PBS—Phosphate Buffer Solution); and
    two cover glasses.

8. A kit for the diagnosis in vitro of the coeliac disease, comprising:
    a test tube containing culture medium of the organ culture type;

a test tube containing the same culture medium as above with the addition of the peptide of gliadin of position 31–43, the aminoacid sequence of which is LEU-GLY-GLN-GLN-GLN-PRO-PHE-PRO-PRO-GLN-GLN-PRO-TYR in the amount of 0.002–0.005 mg/ml;

two glass slides with a section of monkey oesophagus;

a secondary antihuman IGA antibody treated with fluorescin;

washing liquids (PBS—Phosphate Buffer Solution); and two cover glasses.

* * * * *

UNITED STATES PATENT AND TRADEMARK OFFICE
CERTIFICATE OF CORRECTION

PATENT NO. : 5,817,523
DATED : October 6, 1998
INVENTOR(S) : PICARELLI

It is certified that error appears in the above-identified patent and that said Letters Patent is hereby corrected as shown below: On the title page:

Line [30], change "RAM96 A 000523" to --RM96 A 000523--.

Signed and Sealed this

Seventh Day of December, 1999

Attest:

Q. TODD DICKINSON

Attesting Officer

Acting Commissioner of Patents and Trademarks

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( v ) FRAGMENT TYPE: N-terminal ( x i ) SEQUENCE DESCRIPTION: SEQ ID NO:1:

```
      Gln  Gln  Gln  Pro
      1
```

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:2:

```
      Leu  Gly  Gln  Gln  Pro  Phe  Pro  Pro  Gln  Gln  Pro  Tyr
      1                   5                        10
```